United States Patent [19]

Janos

[11] Patent Number: 4,644,272
[45] Date of Patent: Feb. 17, 1987

[54] HOT ANNEALED WELD INSPECTION

[75] Inventor: Wilbert J. Janos, North Ridgeville, Ohio

[73] Assignee: Republic Steel Corporation, Cleveland, Ohio

[21] Appl. No.: 636,301

[22] Filed: Jul. 31, 1984

[51] Int. Cl.$^4$ ............................................. G01N 27/82
[52] U.S. Cl. ...................................... 324/240; 324/228
[58] Field of Search ............... 324/228, 232, 234, 236, 324/237, 238, 239, 240, 242, 243, 225, 226, 227, 224, 233; 148/154; 266/103

[56] References Cited

U.S. PATENT DOCUMENTS

| | | |
|---|---|---|
| 3,057,985 | 10/1962 | Biringer . |
| 3,130,363 | 4/1964 | Camp et al. .......................... 324/224 |
| 3,302,105 | 1/1967 | Libby et al. .......................... 324/233 |
| 3,431,382 | 3/1969 | Esche et al. . |
| 3,588,682 | 6/1971 | Forster . |
| 3,716,908 | 2/1973 | Rowell . |
| 3,753,085 | 8/1973 | Morton et al. . |
| 3,816,690 | 6/1974 | Mittelmann . |
| 3,821,456 | 6/1974 | Havas . |
| 3,825,820 | 7/1974 | Flaherty et al. ..................... 324/227 |
| 4,123,708 | 10/1978 | Vild et al. ............................ 324/224 |
| 4,144,494 | 3/1979 | Pawelletz et al. ................... 324/220 |
| 4,191,922 | 3/1980 | Harris et al. ......................... 324/225 |
| 4,237,419 | 12/1980 | Tornblom et al. ................... 324/225 |
| 4,368,429 | 1/1983 | Jamison ............................... 324/225 |
| 4,387,338 | 6/1983 | Hecht et al. ......................... 324/236 |
| 4,393,598 | 7/1983 | Powell et al. . |
| 4,461,995 | 7/1984 | Harris .................................. 324/224 |
| 4,475,083 | 10/1984 | Linder ............................. 324/239 X |
| 4,562,738 | 1/1986 | Nakayama et al. ................. 324/228 |
| 4,596,953 | 6/1986 | Nagasaka et al. ................... 324/227 |

Primary Examiner—Reinhard J. Eisenzopf
Assistant Examiner—Robert W. Mueller
Attorney, Agent, or Firm—Watts, Hoffmann, Fisher & Heinke

[57] ABSTRACT

An eddy current system and method for hot annealed weld inspection is disclosed for use on metallic workpieces such as steel pipe. An annealer produces strong alternating fields to heat the weld. A nearby exciter coil produces test eddy currents within the workpiece at a carrier frequency. Detector circuitry including a demodulator and a detector coil senses defects within the workpiece as evidenced by nonuniformities in the test eddy currents, in response to which the detector coil produces a flaw indicating signal modulated on the carrier frequency. The carrier frequency is automatically maintained at a non-integral multiple of the annealer alternating frequency. A variable band pass filter between the demodulator and detector coil is automatically maintained with its pass band substantially centered upon the carrier frequency.

38 Claims, 6 Drawing Figures

Fig. 3
SIGNAL VERIFIER CIRCUIT

HOT ANNEALED WELD INSPECTION

DESCRIPTION

1. Technical Field

This invention relates to the field of non-destructive eddy current testing of metallic workpiece product such as welded steel pipe whose weld seam has been annealed by induction heating apparatus. More specifically, the invention relates to apparatus and method for effecting on-line eddy current testing of annealed pipe welds at a location close to the annealer and at which the temperature of the tested weld region remains above its Curie temperature, while avoiding undesirable response to interference from strong annealing electromagnetic fields.

2. Background Art

This invention relates to the making of pipe. A common method of manufacturing pipe begins with strip steel product. The strip product is fed longitudinally through a station in which it is mechanically formed into a generally elongate cylindrical shape. After forming, a longitudinal seam defined by adjacent edges of the formed strip is closed by welding.

The welding process produces at the weld seam a region of metal different in crystalline structure and physical properties from the metal constituting the remainder of the pipe wall. Often, the metal in the weld seam region, or bead, is undesirably brittle and subject to fracture.

In order to correct this deficiency, an annealing, i.e. heating, process is used to normalize the crystalline structure of the metal in the weld area with respect to the metal constituting the remainder of the pipe wall.

After welding, the pipe is propelled through a series of annealing stations to effect the normalizing process. Each annealing station includes a single high current annealing coil positioned proximate the weld seam or bead as the pipe passes by. The annealing coil is coupled to an alternating power source which drives a high alternating electrical current through the annealing coil. The alternating current produces a strong alternating electromagnetic field in the region of the pipe weld. This alternating field induces strong eddy currents in the region of the weld and results in considerable heating of the weld.

The pipe is passed through the series of annealing stations in rapid succession, such that, in passing the series of stations, the temperature of the weld region is successively raised, in increments, until, having passed the final annealing station, the weld region has attained a temperature of between 1400° and 1900° F.

Typically, the frequency of the alternating electromagnetic fields employed in this induction annealing process is between 700 and 1100 Hz. An annealing apparatus suitable for pipe weld annealing can comprise a Type 3 annealer made by Tocco Corporation, of Cleveland, Ohio, U.S.A.

It is desirable to nondestructively test the quality, i.e., degree of freedom from flaws, of the annealed welds. It is preferable that the testing be done on the pipe production line itself, close to the annealers, so that corrective measures can be taken as promptly as possible when a defect occurs, to minimize the amount of flawed product produced.

One method of such flaw detection employs eddy currents. In a known type of eddy current flaw detection station, three coils are used: an exciter coil, a detector coil and a saturation coil. A power source coupled to the exciter coil produces a small alternating electrical current in the exciter coil, at a test, or "carrier" frequency. The exciter coil is located proximate the pipe or other workpiece to be tested, and induces test eddy currents in the pipe as it passes the coil.

The detector coil is located near the exciter coil.

In the absence of flaws, these test eddy currents remain substantially uniform as a pipe is propelled past the eddy current detection station. When a flaw passes the detector coil, however, the presence of the flaw causes changes in the eddy currents generated in the region of the pipe near the flaw. The variation, or modulation on the carrier frequency by the flaw indicating signal, is sensed by the detector coil, which is coupled to demodulating circuitry and apparatus for producing an indication of the detected flaw.

The saturation coil may encircle the pipe and receives a relatively large D.C. current from a power source, producing a relatively large and non-varying magnetic field in the region including the pipe near the exciter and detector coils. The magnetic field produced is sufficiently large to magnetically saturate the workpiece region of interest such that it exhibits paramagnetic, rather than magnetic, properties. The paramagnetic condition produced in the workpiece enhances the response of the detector coil to the passage of flawed pipe regions.

Examples of eddy current detection systems are described in U.S. Pat. Nos. 4,191,922 and 4,123,708, issued on Mar. 4, 1980 and Oct. 3, 1978, to Richard M. Harris, et al, and to Vild, et al, and which are hereby expressly incorporated by reference.

It has in the past been required to locate eddy current annealed weld flaw detection stations many (20-150) feet downstream from the final annealing station. A reason for this requirement is that the induction annealing fields are approximately one million times stronger than the eddy current test fields.

The eddy current test system must be remotely spaced from the annealer to avoid interference from the induction annealing fields which are sufficiently strong to swamp out and effectively disable operation of the eddy current detection operation employing the much lower test field strengths.

Several disadvantages flow from the necessity for widely separating the annealing and detection stations. A product defect is not detected under such conditions until a large quantity of additional and possibly flawed product will have been run.

If the product flaw were detected earlier, corrective measures, if needed, could be promptly initiated, and the amount of defective product could be substantially reduced.

Another disadvantage of separating the detection and annealing stations is that, by the time the product reaches the detection station, it has cooled considerably from its annealing temperature. Generally speaking, the annealing temperature is above the Curie point (about 1300° F.) of the steel pipe product, the point at or above which the pipe exhibits the desirable paramagnetic properties. When eddy current flaw detection is employed on product whose temperature is below the Curie point, the special saturation coil described above must be used for effective detection. A saturation coil, which must produce a strong D.C. magnetic field to continuously magnetically saturate the product at the test region, consumes considerable electrical energy. Moreover, the required presence of the saturation coil itself adds considerably to the bulk and expense of the eddy current detection apparatus.

It has been proposed in eddy current flaw detection systems, to interpose electrical filters, including band pass filters, at appropriate locations in the test circuitry. This is said to reduce noise caused by potentially interfering electromagnetic fields.

Such filters, however, do not enable reduced separation between the eddy current testing equipment and many types of annealer equipment, which employ a variable frequency annealing current.

More specifically, some newer types of annealing apparatus employ solid state electrical power sources, whose frequency is relatively easy to adjust. Frequency adjustability is used as a primary means of regulating power imparted in the induction annealing process. In such systems, the annealing frequency, to maximize power, is tuned to the resonant frequency of the annealing circuit. In order to reduce the power applied, the frequency is detuned away from the resonant frequency, with the result that, the greater the increment between the actual frequency and resonant frequency, the less power is transmitted.

Normal electrical filtration techniques in eddy current flaw detector apparatus are not suitable for minimizing noise and interference from the annealer where the annealer frequency varies, since the electrical filters have fixed pass bands.

It can be seen from the foregoing discussion that it is desirable to monitor the temperature of the pipe weld region in order to continuously confirm the proper operation of the annealing apparatus. It has been proposed to accomplish this by the use of a conventional temperature detecting device, such as a thermocouple. These devices, however, will in time deteriorate and malfunction because of the necessity for their continuous exposure to extreme temperatures.

Another problem encountered in eddy current flaw testing relates to discrimination between flaws which are harmful to the product structure, and other irregularities which, while not particularly harmful to the product itself, sometimes nonetheless produce eddy current variations which are detected, thereby cause a spurious flaw indication.

It is also desirable to be able to detect not only individual nonuniformities in eddy currents, but also series of discrete but similar irregularities causing a series of flaw indicating signals over a period of time. It is desirable because some types of malfunction in the pipe making process give rise to series of repetitive discrete irregularities over an extended period of time, and it is beneficial to be able to detect and identify those repetitive series of discrete irregularities in order to facilitate choice and application of the proper corrective measures.

It is an object of this invention to provide an eddy current flaw detector which is capable of effective operation even when positioned proximate a high power, variable frequency induction annealer, and which can monitor weld temperature, flaw signal characteristics and patterns of recurrent flaws.

DISCLOSURE OF INVENTION

The disadvantages and problems of the prior art as explained above are reduced or eliminated by the hot annealed pipe weld flaw detection system and method of this invention.

The system is designed for use in connection with welded pipe manufacturing apparatus which includes an apparatus for induction annealing of pipe welds. The annealing circuitry produces strong alternating electromagnetic annealing fields in the region of the pipe weld, as pipe is moved past the annealers, raising the temperature of the weld region to a level sufficient to anneal the pipe welds by normalizing the crystalline structure of the weld area with respect to that of the pipe wall.

The system includes an exciter coil coupled to exciter circuitry for generating relatively small alternating test eddy currents in the weld region of the pipe at a carrier, or test, frequency. These test eddy currents are different from the much stronger currents generated in the pipe weld area in the induction annealing process. The system also includes apparatus for propelling the pipe past the exciter circuitry, and detection circuitry responsive to variation in the test eddy currents to produce a signal indicating a defect in the pipe.

The annealing circuitry includes circuitry for varying the frequency of the induction annealing electromagnetic fields. Circuitry coupled between the annealing circuitry and the exciter circuitry adjusts automatically the alternating carrier frequency of the test eddy currents as a function of the induction annealing field frequency.

The adjustability of the eddy current test carrier frequency enables the system to continuously maintain the carrier frequency sufficiently far removed from the annealing frequency to reduce interference, in the exciter and detection circuitry, from the strong annealing fields. This resistance to interference from the annealing fields permits the eddy current flaw detection system to be placed quite close to the annealing apparatus and circuitry, to facilitate the earliest possible detection of flaws in the pipe product and to thereby minimize the amount of potentially flawed product which would be greater if flaws were not located until they had progressed a relatively long distance subsequent to annealing.

In accordance with a more specific aspect of the invention, the test eddy current carrier frequency is continuously maintained as a non-integral multiple of the induction annealing field frequency. Tests have shown that a particular interference resistant test carrier frequency is approximately 4.5 times the induction annealing field frequency. Additionally, tests have shown that the eddy current test system is most resistant to interference from the annealers if the test carrier frequency is maintained approximately equally spaced between successive harmonics of the annealing field frequency.

In accordance with another aspect of the invention, the detection circuitry includes a demodulator, and a variable band pass electrical filter in series ahead of the demodulator, to further reduce the effects of interference in the detection circuitry. A more specific feature of the invention is embodied in the provision of frequency control circuitry which senses carrier frequency and maintains the pass band of the adjustable filter centered approximately on the carrier frequency as the carrier frequency varies as described above.

According to another aspect, the flaw detection system includes a supplemental ultrasonic pipe testing system for providing additional flaw detection capability.

According to another specific feature, verification circuitry is coupled to receive signals, and to produce an output only in response to those flaw indicating signals having certain predetermined characteristics. In this way, the system discriminates between irregularities in the pipe weld which do not materially affect product quality, or transients not indicating defects at all, and those irregularities which do require corrective action to assure proper integrity of the product.

Another feature of the invention is embodied in the detection coil comprising a differentially wound coil which is coaxial with the exciter coil, the axis of both coils extending parallel to the pipe axis as the pipe moves past the coils. Tests have shown that this particular coil configuration is most sensitive for detecting flaws in the weld area.

According to another specific feature, the system includes circuitry responsive to the output of the detector coil for indicating temperature of the weld area. More specifically, this temperature indicating circuitry responds to changes in the degree of imbalance exhibited by the differentially wound detector coil, a phenomenon which indicates resistivity, and hence temperature, of the pipe. This feature produces a warning or indication if the temperature of the tested weld area falls below its Curie temperature, a decrease which, if allowed to persist, would interfere with testing in that the eddy currents would not penetrate as well below the Curie temperature, and the system would become subject to nonuniform magnetic properties of the pipe.

These and other features of the present invention will become apparent from the following detailed description and from the drawings, in which:

BEST MODE FOR CARRYING OUT THE INVENTION

Figure 1:
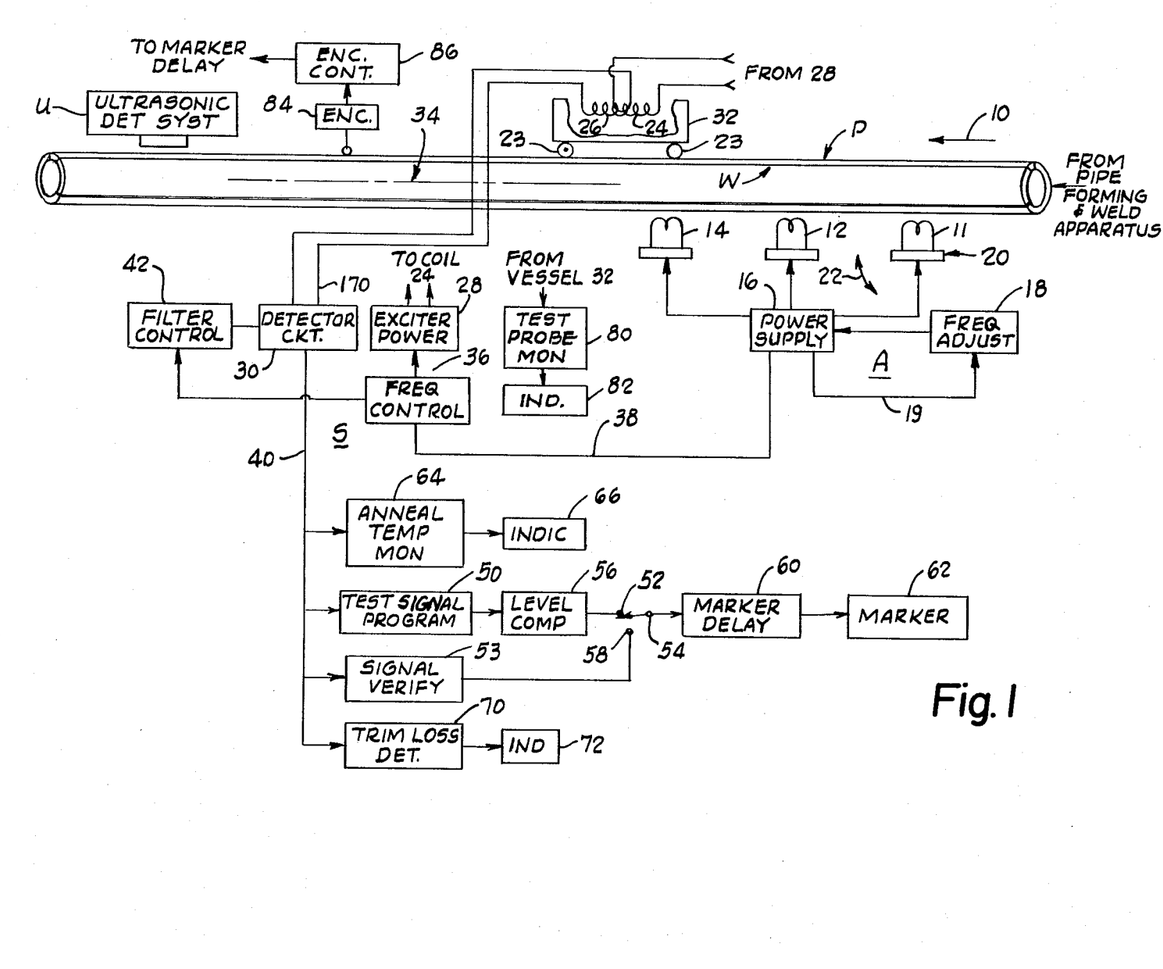
FIG. 1 is a partially pictorial, partially block diagram illustrating a system incorporating the present invention.

FIG. 1 illustrates annealing apparatus and circuitry A for heat treating a weld bead or seam W of a welded pipe P moving in a direction indicated by an arrow 10. FIG. 1 also illustrates an eddy current flaw detection system S downstream from the annealer for detecting flaws or defects in the region of the weld seam W of the pipe P. Downstream from the eddy current detection system S is an ultrasonic detection system U, of known type, which performs further tests on the integrity of the pipe P by the use of ultrasonic energy.

The pipe P is formed by means of known pipe forming apparatus (not shown). The pipe forming apparatus receives a piece of relatively narrow, strip steel material, which is moved longitudinally through the forming apparatus. In the course of this movement, the forming apparatus forms the strip material into a generally cylindrical shape, such that its side surfaces are curved toward one another until they are adjacent, and form the site for welding the formed material into pipe product. Pipe welding apparatus operates to weld the now adjacent surfaces together to form an elongated weld seam or bead W extending longitudinally along the pipe.

The annealing system A includes a series of annealing coils 11, 12, 14, a power supply 16 and frequency adjustment circuitry 18. Each of the annealing coils 11, 12, 14 consists of a single coil of relatively heavy electrically conductive material, such as copper, which is located proximate the weld seam W running along the top of the pipe P as shown in FIG. 1. The coils 11, 12, 14 are positioned relatively close together along the pipe path as defined by the arrow 10.

The power supply 16 supplies large amounts of electrical energy to each of the coils 11, 12, 14, at an alternating frequency which is adjustable between approximately 700 and 1100 Hz. As a particular section of the pipe weld seam W passes along the path as defined by the arrow 10, it passes near coils 11, 12, 14 in rapid succession. The relatively high power flowing through each of these coils generates strong electromagnetic fields in the region of the pipe weld passing by the respective coil. These strong alternating fields produce large eddy currents in the pipe weld region, which anneal the pipe weld and normalize the crystalline and physical properties of the weld region with respect to the metal comprising the remainder of the pipe wall.

As a given segment of the pipe weld W sequentially passes by each of the annealing coils 11, 12, 14, its temperature is raised incrementally by a considerable degree, due to the large input of energy by induction from the coils. By the time the pipe weld segment has passed by the final coil 14, its temperature is in the approximate range of 1400°–1900° F. This annealing temperature is above the Curie point for the pipe metal, the temperature at or above which the pipe begins to exhibit paramagnetic, rather than the normal magnetic, properties.

The output of the power supply 16 to the coils 11, 12, 14 is adjustable. The output is adjusted by regulating the frequency of the power supply 16. Preferably, the power supply 16 comprises a solid state power source, the frequency of operation of which is relatively easily adjustable.

Frequency adjustment circuitry 18 is employed, in connection with feedback, to regulate the power output of the supply 16.

For maximum power, the supply 16 is adjusted to impart electrical energy to the coils at approximately the resonant frequency of the annealing circuitry, including the coils, and as affected by the presence of the pipe P near the coils. In order to reduce the power as desired, the frequency output by the power supply 16 is detuned from the resonant frequency by an amount sufficient to accomplish the desired power reduction. Closed loop feedback, as indicated as passing over a lead 19, is utilized to cause the power supply and frequency adjustment circuitry 18 to cooperate to automatically maintain a given induction annealing power output.

Provision is made for displacing the coils 11, 12, 14 from the path of the pipe P when desired, as about a pivot 20, shown in connection with coil 11. Such displacement is desirable when the leading or trailing edge of a pipe run is passing by the coils. Displacing the coils from the pipe path during such times is advantageous because the pipe forming apparatus sometimes fails to close the pipe completely near the leading or trailing edges of the strip material used as the precursor for the pipe. If the coils were not so displaced, they could be damaged by protruding edges of the incompletely formed precursor material.

The annealing system A is suitably embodied by an annealing apparatus Type 3 (modified), manufactured by Tocco, of Cleveland, Ohio, U.S.A.

The eddy current detection system S includes an exciter coil 24, a detector coil 26, an exciter power supply 28, and detection circuitry 30. The coils 24, 26 are at least partly enclosed within a vessel 32, made of nonmagnetic stainless steel, which is adapted for containing a liquid coolant to control the temperature at which the coils 24, 26 must operate, in view of their proximity to the hot weld region W of the pipe P. The vessel 32 rides atop the pipe on rollers 23, supporting the vessel about 0.030 inches above the pipe.

The coils 24, 26 define rectangular cross-sections and are wound about the same axis which is parallel to the axis 34 of the pipe P. The detector coil is wound on top of the exciter coil. The detector coil 26 preferably comprises a pair of series differentially wound coils such as illustrated in FIG. 1 of the referenced Harris et al patent and functions in a manner analogous to that explained in that patent.

The exciter coil 24 receives power from the exciter power supply 28, and, in response, generates eddy currents at the carrier frequency in the weld region of the pipe P. These eddy currents, however, are only about one millionth as large as the eddy currents generated by the induction heating apparatus A.

The exciter and detector coils 24, 26, are positioned within a few feet downstream of the final induction annealing coil 14.

Frequency control circuitry 36, coupled between the annealer power supply 16 and the exciter power supply 28, adjusts the frequency of the alternating current in the exciter coil 24 as a function of the annealing frequency produced by the power supply 16. A signal appearing at a lead 38 is input from the annealer power supply to the frequency control circuitry 36, representing the annealer frequency. In response, the frequency control circuitry 36 adjusts the exciter power supply 28 to produce an alternating electric current in the exciter coil 24 which is a function of the annealer frequency.

More specifically, the exciter frequency is maintained as a non-integral multiple of the annealer frequency. Preferably, the exciter frequency constantly tracks the annealer frequency at a value of 4.5 times the annealer frequency.

Maintenance of the exciter frequency, and hence of the test eddy current frequencies, at 4.5 times the annealer frequency permits placement of the eddy current detector system S relatively close (within 18 inches) to the annealer system A, by substantially reducing the susceptibility of the eddy current system S to interference from the very strong induction annealing fields.

The detector coil 26, positioned near the weld seam W as the pipe progresses along its path, detects and produces a voltage, modulated on the carrier, in response to variations or nonuniformities in the eddy currents produced in the pipe weld region by the exciter coil 24. In instances in which the detector coil 26 is differentially wound, it will be sensitive to, and produce a voltage, only in response to variations in the eddy currents, and will not produce an output in response to continuous electromagnetic noise fields encompassing the entire coil.

The output of the detector coil 26 is coupled to the detector circuitry 30. The detector circuitry 30 senses the voltage appearing across the detector coil terminals in response to nonuniform eddy currents, which indicate flaws, and produces an output at a lead 40 indicating the passage of a defect past the detector coil 26. The signal appearing at the lead 40 is utilized in a number of ways which will be described in more detail below.

Additional means is provided in the detector circuit 30 for further reducing interference from the annealing fields. This means includes an adjustable electrical filtration means 41 located within the detector circuitry, as will be described in more detail below. Filter control circuitry 42 is interposed between the frequency control circuitry 36 and the detector control circuitry 30. In response to a signal from the frequency control circuitry 36 representing the exciter carrier frequency (which is preferably 4.5 times the annealer alternating field frequency), the filter control circuitry 42 operates to adjust the variable filter means 41, a digital band pass filter, within the detector circuitry 30. More specifically, the variable filter means is adjusted to provide a pass band for excluding from the detector circuitry frequencies differing considerably from the exciter carrier frequency. The filter control circuitry 42 adjusts the center point of the pass band to coincide with the exciter carrier frequency value, and maintains that adjustment notwithstanding variations in the exciter frequency itself.

The output of the detector circuit, appearing on the lead 40, is directed in parallel to a signal test processing circuit 50 and a signal verification circuit 53. The output of the signal test programming circuitry is directed to one pole 52 of a switch 54 by way of a level comparator 56. The output of the signal verification circuitry 53 is connected to the other pole 58 of the switch 54.

The output of the switch 54 is transmitted to a marker delay circuit 60, which in turn actuates a marker 62.

The marker 62 applies a mark on the portion of the pipe P at which a defect was sensed. The marker delay circuit 60 delays actuation of the marker 62 for a time which is equal to the time required for the defect to pass from the detector coil 26 to the marker 62.

The switch 54 provides for selective actuation of the marker delay by the output of the level comparator 56 or of the signal verification circuitry 53. When the switch 54 is positioned to contact the pole 52, only defect signals having a level at least equal to a predetermined value are accepted for actuating the marker delay circuitry 60 and the marker 62. When the switch 54 contacts the pole 58, the marker delay and paint marker respond only to signals in response to which the signal verification circuitry 53 produces an output.

The test signal program circuitry and level comparator circuitry 56 cooperate to produce an output of the level comparator 56 only when the defect signal appearing on the lead 40 is equal to or greater than a predetermined minimum.

The signal verification circuitry 53 produces an output only when the defect signal appearing at the lead 40 has a waveform which has a predetermined polarity sequence, or "signature".

By operation of the level comparator 56 and signal verification circuitry 53, the eddy current test system can be preset to respond only to defect signals having predetermined waveform characteristics. Thus, the eddy current detection system can discriminate between certain types of defect signals to which a reaction is desired, and the circuitry will ignore signals which indicate minor irregularities in the pipe, or transients, which are not of sufficient magnitude, or of the type, to indicate flaws deemed to significantly degrade the pipe product.

Figure 3:
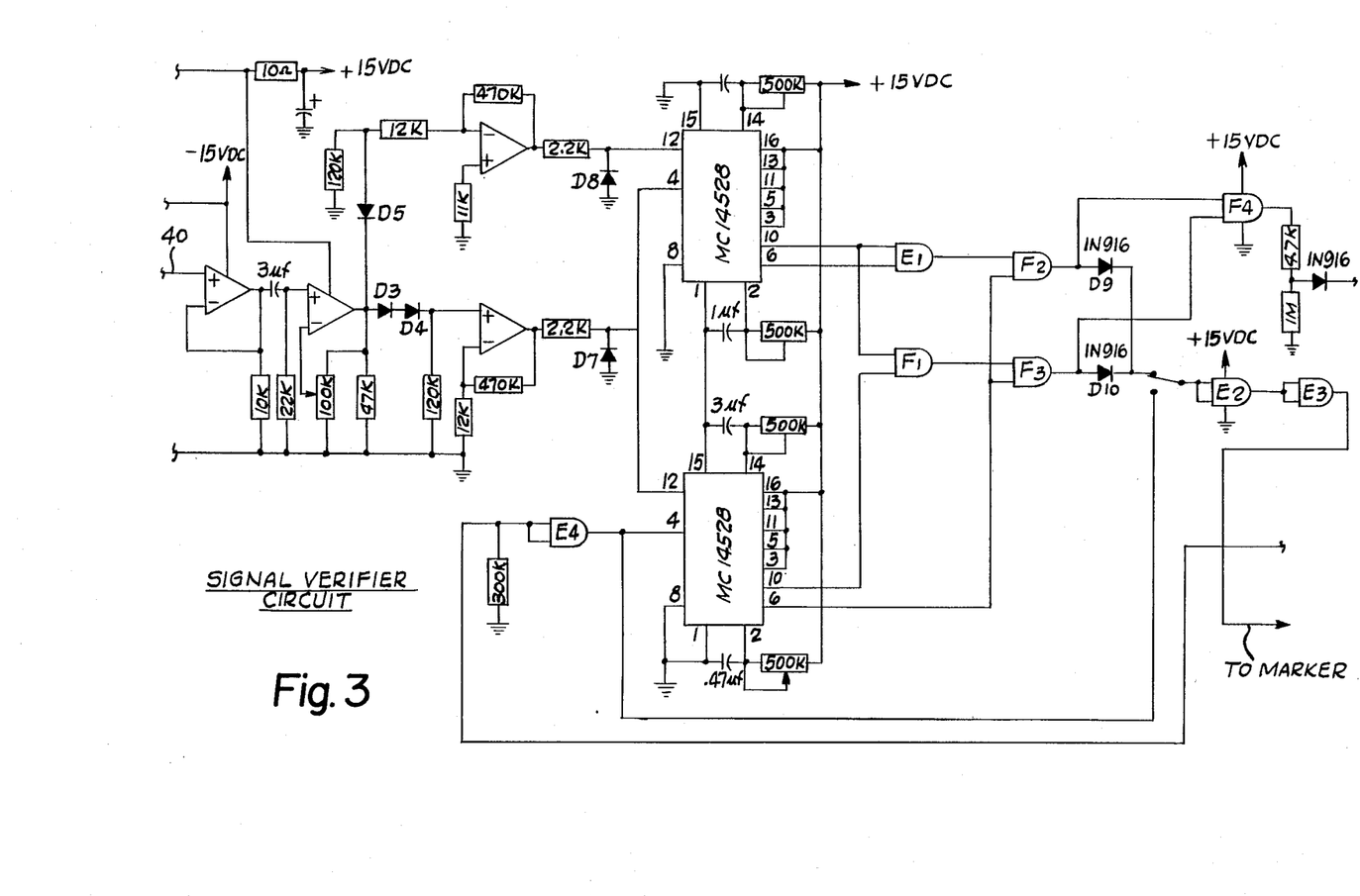
FIGS. 3–5 are schematic drawings illustrating components of the embodiment of the invention shown in FIG. 2.

The signal verification circuitry is illustrated in schematic form in FIG. 3. The level comparator 56 and programming circuit 50 are analogous to circuitry described in U.S. Pat. No. 3,916,301, issued Oct. 28, 1975, here expressly incorporated by reference, especially in connection with FIG. 2 thereof, and the accompanying description.

Figure 3A:
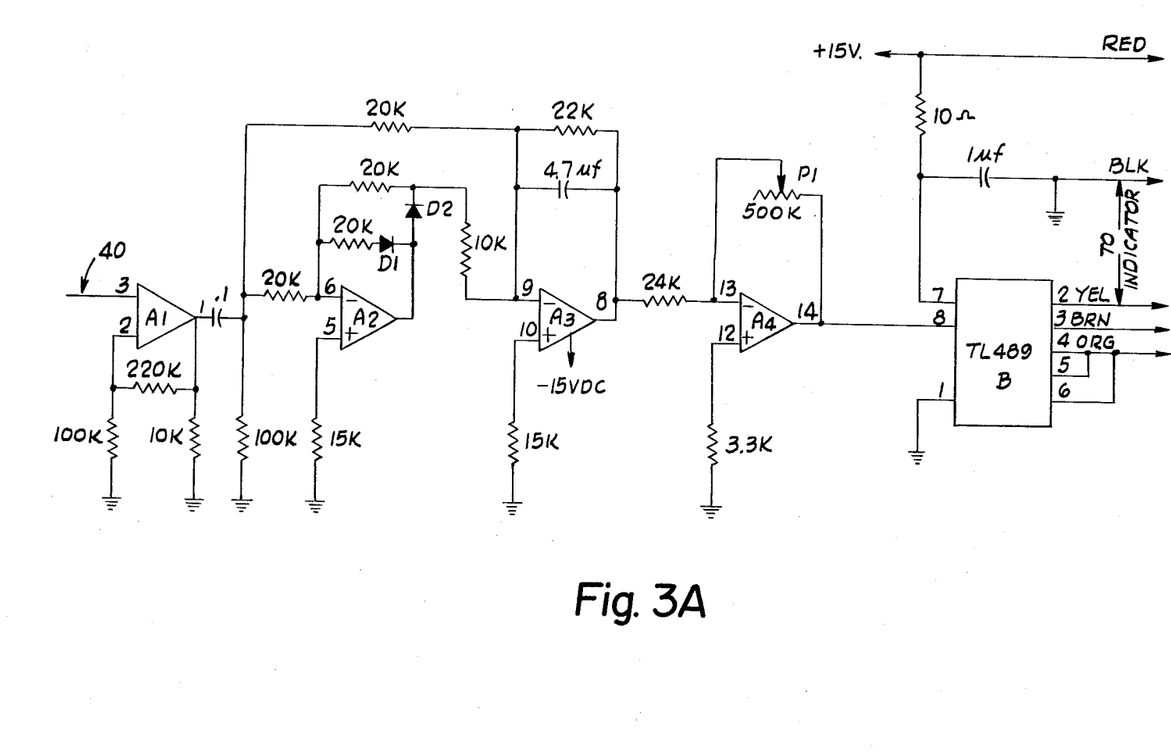

The output of the detector circuit 30, appearing on the lead 40, is also directed in parallel to an annealing temperature monitor circuit 64. The anneal temperature monitor is schematically shown in FIG. 3a. The temperature monitor circuit 64 senses the temperature of the pipe weld region passing the detector coil 26 by sensing the amount of imbalance in the detector coil indicated by the defect signal appearing at the lead 40. This degree of imbalance indicates the resistivity of the pipe weld region near the detection coil, which in turn is a function of the temperature of the weld region. If the signal at the lead 40 indicates a sufficient amount of imbalance, such that the temperature indicated is at least a predetermined value, i.e., the Curie temperature, no output appears at the anneal temperature monitor 64. If, however, the signal characteristics at the lead 40 indicate that the temperature of the weld region passing by the detector coil 26 has fallen below its Curie point, an indicator 66 is actuated to advise an operator of the need for correction and the increase of power to the induction annealing coils, and the marker delay circuit 60 is actuated.

Finally, the signal at the lead 40 is transmitted in parallel to trim loss detection circuitry 70. The trim loss detection circuitry detects a lack of proper removal (trim) of an inside diameter mold band used in making the pipe.

In the pipe manufacturing process prior to annealing, should the I.D. trim tool malfunction, the result will be the occurrence of a succession of discrete, substantially equally spaced irregularities i.e. weld puddles along the inner wall of the pipe. Such a phenomenon results in the production of a lengthy series of defect signals at the lead 40 which occur as the pipe section incorporating the band irregularities passes by the detector coil 26. This phenomenon differs from other types of irregularities, which commonly occur at random, and which typically produce only a single defect indicating signal.

Figure 4:
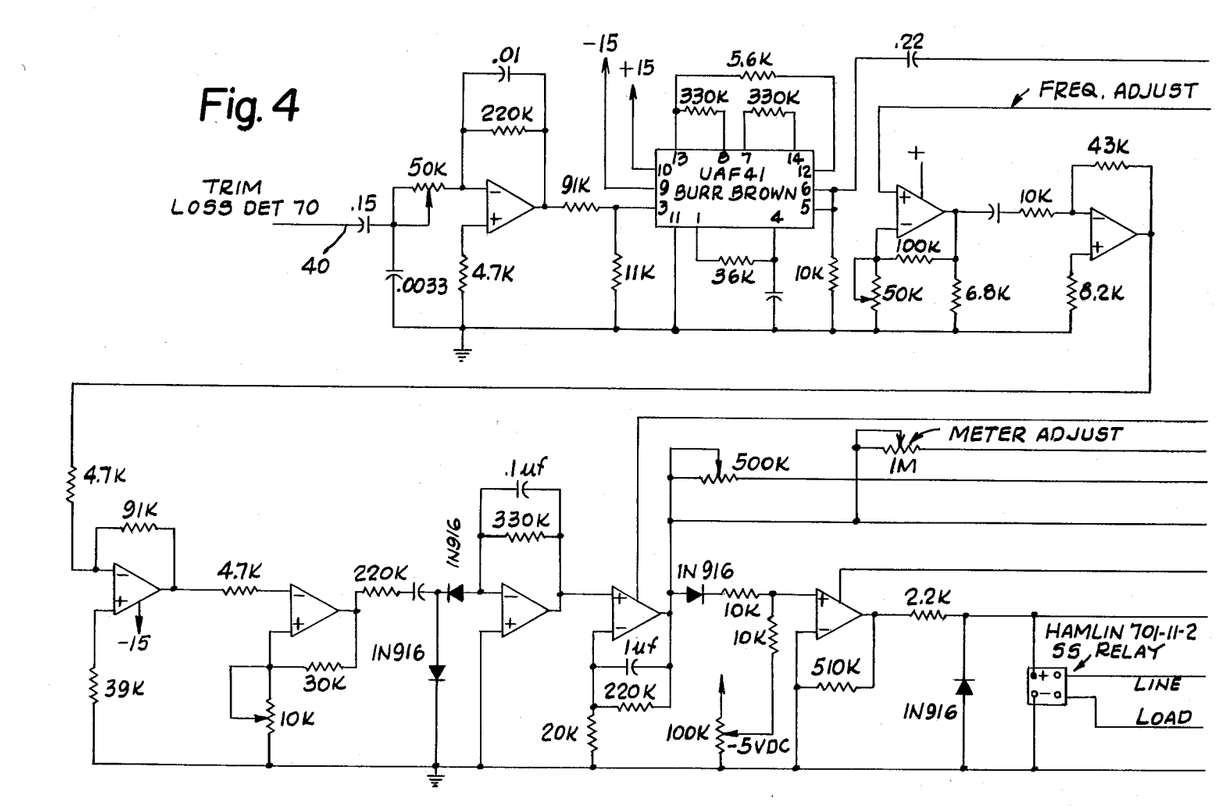

The trim loss detector 70 (see FIG. 4 for a schematic diagram) responds to the succession of approximately regularly spaced defects, and regularly spaced defect indicating signals, to produce a recurrent flaw signal. The trim loss detector 70 produces a recurrent flaw signal at its output only upon the receipt of a series of defect indicating signals having a frequency of approximately 30–90 Hz. for a predetermined time of approximately one second. In response to an output at the trim loss detector 70, an indicator 72 provides an indication that proper I.D. trim is not occurring, which immediately warns an operator of the existence and nature of the defect, enabling him to institute corrective measures.

The eddy current flaw detector system S also includes a test probe monitor 80 and indicator apparatus 82. The test probe monitor 80 receives a signal from a sensor (not shown) which detects whether the coolant level in the vessel 32, in which the detector and exciter coils are located, is below a predetermined level. In response to the coolant falling below a predetermined level, the test probe monitor 80 produces an output to the indicator 82 which immediately warns of this potentially damaging condition, and prompts an operator to restore the coolant level in the vessel 32.

The coolant level sensor can be embodied by a simple DC circuit whose contacts are normally both immersed in the coolant, but, when the coolant falls below a predetermined level, the circuit is broken, actuating the indicator 82.

Alternately, sensing means, such as a thermocouple, can be immersed in the coolant in the vessel 32 in order to monitor the temperature of the coolant, such that, when the temperature exceeds a predetermined value, an indication is produced.

Figure 5:
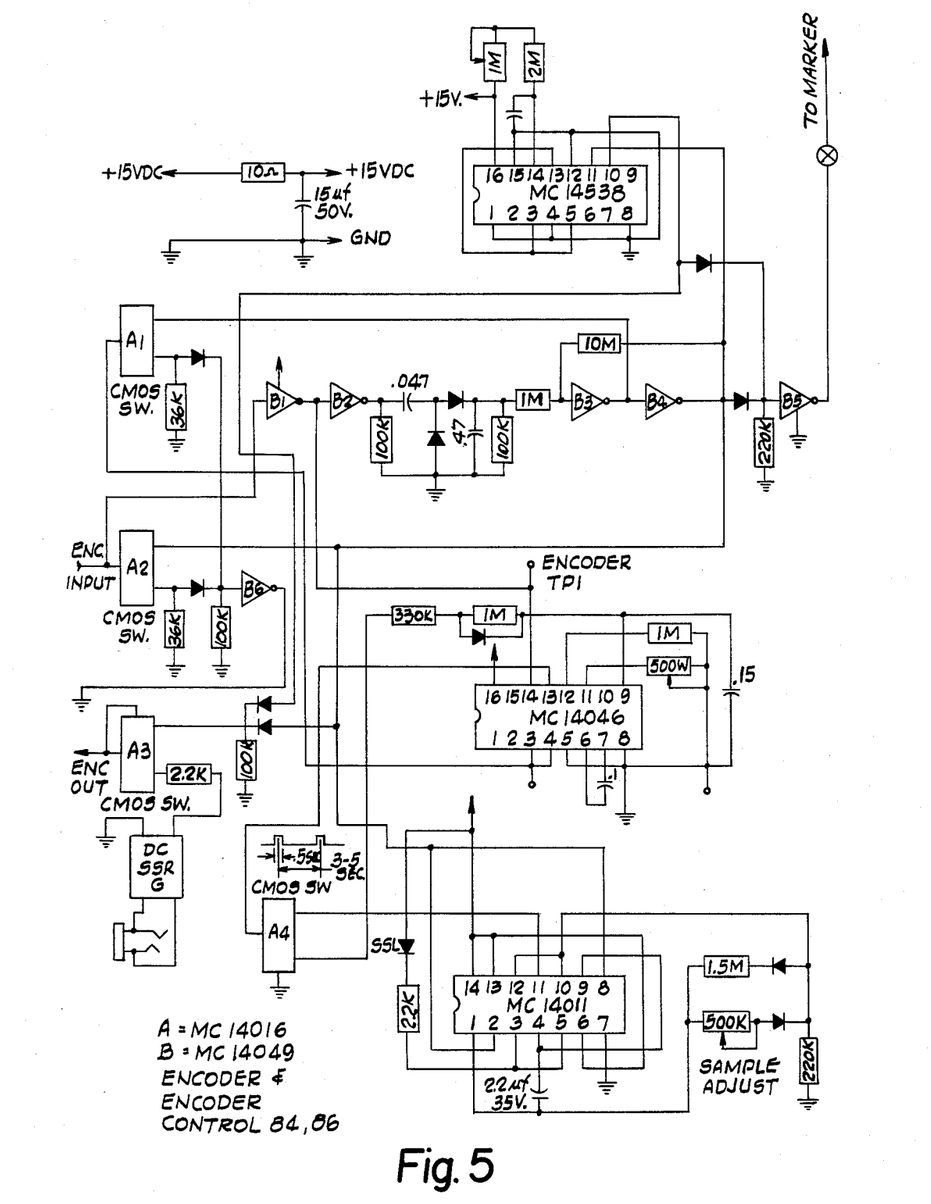

Encoder circuitry 84 and encoder control circuitry 86 are also provided. The encoder circuitry 84 comprises a photo-optical encoder device having a wheel which is engageable for rolling along the pipe, and means for sensing the speed of rotation of the wheel, and hence the speed at which the pipe proceeds along its path indicated by the arrow 10. The encoder circuitry 84 produces a series of pulses at its output which is directly proportional to the speed of pipe movement. The encoder control circuitry 86 (see FIG. 5) receives the output from the encoder 84, and produces a signal at its own output, which is directed to the marker delay circuit 60. The output of the encoder control circuit 86 adjusts the time delay imposed by the marker delay circuitry 60. This delay adjustment adjusts the paint marker delay to compensate for any changes in speed of the pipe motion. For example, if the pipe slows down, a flawed region will take longer to pass from the detector coil 26 to the paint marker 62, and consequently, the desired marker delay will increase. As pipe motion increases, the time for transit between detector coil and paint marker will decrease, and it will be desirable to reduce the marker delay time correspondingly.

Figure 2:
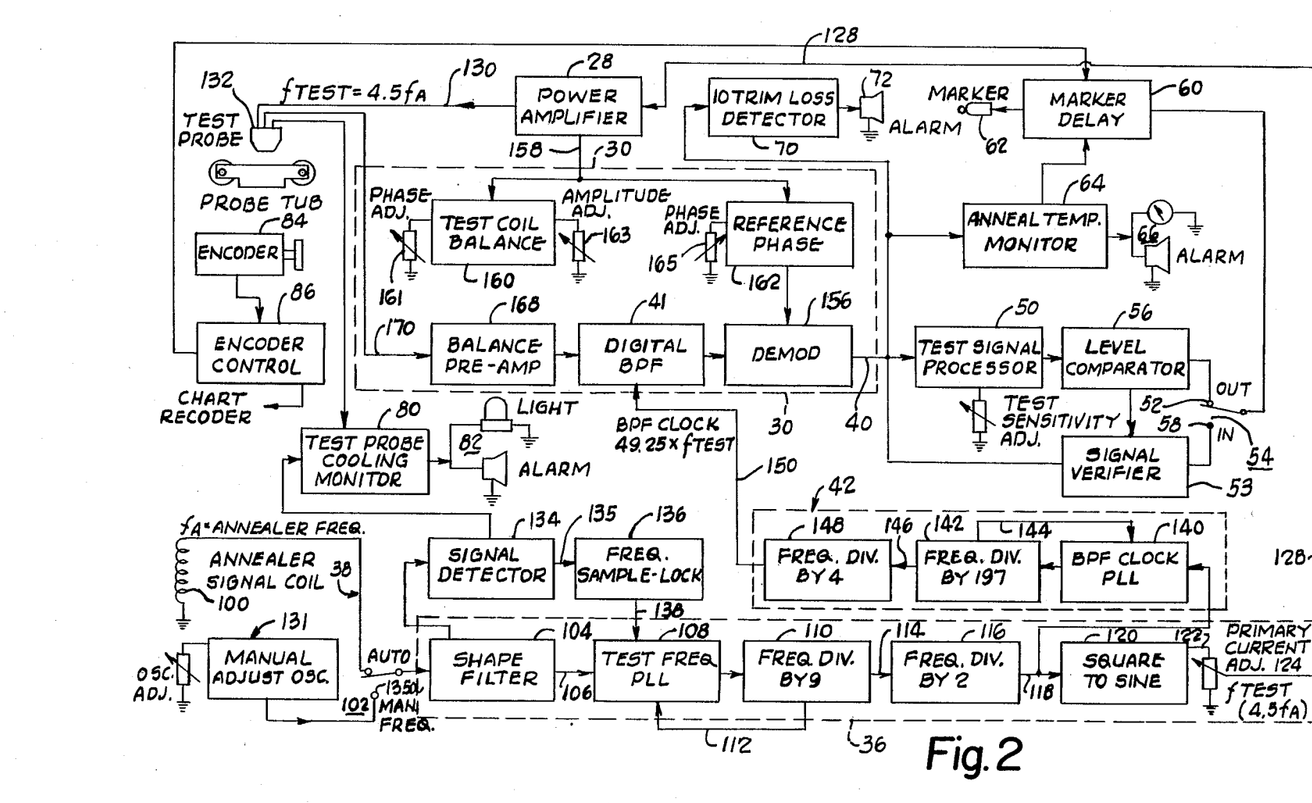
FIG. 2 is a more detailed block diagram illustrating a portion of the embodiment illustrated in FIG. 1.

FIG. 2 shows the eddy current test system S in block form and in greater detail. FIG. 2 illustrates the frequency control circuitry 36 and its means of coupling to the power supply 16 of the annealing apparatus and circuitry.

An annealer signal coil 100 is located proximate the annealing circuitry and produces a signal upon the lead 38 which is an alternating signal having the same frequency as that of the annealing circuitry. The signal on the lead 38 is normally transmitted by way of a switch 102 to a shaping filter 104. The shaping filter 104 converts the signal from the coil 100, which is normally approximately a sine wave, or another wave having a relatively high rise time, to substantially a square wave at the output 106 of the shaping filter 104. The filter 104 comprises 2 band pass filters, a buffer amplifier and a zero cross detector, and is of a known type which can readily be provided by one of ordinary skill.

The annealing frequency, transmitted as a square wave on the lead 106, is input to a phase lock loop 108, comprising an integrated circuit chip designated MC 14046. The output of the phase lock loop 108 is directed to a divide by 9 circuit 110, comprising an MC 14017 chip. An output of the divide by 9 circuit is directed by way of a lead 112 to feed back to the phase lock loop 108. Together, the phase lock loop 108 and the divide by 9 circuit 110 produce, at an output 114, a signal having a square waveform and having a frequency 9 times that of the annealing frequency originally sensed by the annealer signal coil 100. The output 114 is then passed through a divide by 2 circuit 116. The output of the divide by 2 circuit is a square wave having a frequency of 4.5 times the annealing frequency, and this output appears at a lead 118.

An output from the divide by 2 circuit 116 is transmitted to the input of a square to sine converter 120, comprising an NE 570 compander, which converts the square wave to approximately a sine wave having a frequency of 4.5 times the annealer frequency, which signal appears at an output 122. After a passing through a primary current adjusting potentiometer 124, the sine wave having a frequency of 4.5 times the annealer frequency is transmitted over a lead 128 to the exciter power amplifier 28. After amplification, this exciter carrier signal is transmitted over a lead 130 to the test probe assembly 132, where it is coupled to power the exciter coil 24 (not shown in FIG. 2) in accordance with the description given above.

The frequency control circuitry 36 also includes a signal detector 134 and a frequency sample-lock circuit 136. The signal detector 134 receives an input from the shape filter 104. The signal detector in known fashion converts the sensed frequency from the shape filter to a DC signal proportional to the frequency. The signal detector thus can sense annealer turn on. The signal detector circuit additionally has delay circuitry wherein the signal detector delays for 15 seconds after sensing annealer turn on prior to producing an output at a lead 135.

The output of the signal detector 134 is transmitted to the frequency sample lock circuit 136. The frequency sample lock circuit 136 comprises a C-MOS circuit including chips MC 14538 and MC 14066, and comprises an analog switch, producing a DC level output over a lead 138 to control turn on of the phase lock loop 108. Thus, the delay imposed by the signal detector and frequency sample lock circuits allows the annealing circuitry a sufficient length of time to settle prior to turning on the frequency control circuitry 36 by actuating the phase lock loop 108, which is the primary frequency synthesizer.

A manual frequency adjust oscillator 131, of known type, together with an adjusting potentiometer 133, is provided for use in conjunction with the frequency adjustment circuitry. When the switch 102 is moved to contact the terminal 135a, the output of the oscillator 131, rather than the output of the coil 100, is directed as an input to the shaping filter 104. Adjustment of the potentiometer 133 adjusts the frequency output of the manual oscillator 131. In this way, when desired, the manual oscillator can be used to establish manually the exciter test frequency, such as when a constant frequency annealer current is utilized, or when for some other reason it is desired to utilize an exciter frequency of other than 4.5 times the annealer frequency.

It should be pointed out that suitable results can be obtained by utilizing a test frequency which is a non-integral multiple of the annealer frequency, other than the multiple of 4.5. The multiple of 4.5 is preferred, though, for its good compromise beween efficiency and eddy current penetration. Thus, 3.5, 5.5, 6.5 etc. multiples can be used. It is desirable, however, that the frequency multiple embodied in the exciter test signal be approximately centered between successive harmonics of the annealer frequency. Thus, tests have shown, for example, that the use of a multiple of 4.5 for the test signal is superior to the use of a multiple of 4.1 or 4.9.

FIG. 2 also illustrates the filter control circuitry 42. The filter control circuitry 42 includes a phase lock loop 140 and a frequency divide by 197 circuit 142, which is coupled by way of a lead 144 to feed back to the phase lock loop 140. Together, the phase lock loop 140 and divide by 197 circuit 142 combine to produce a signal at a lead 146 which is a square wave in configuration and has a frequency of 197 times the exciter frequency produced at the divide by 2 circuit. The signal at the output 146 is then transmitted through a divide by 4 circuit 148, which produces, at a lead 150, a clock pulse which is a square wave having a frequency of 49.25 times the frequency appearing at the output 118 of the divide by 2 circuit 116.

The clock signal appearing at the lead 150 is directed as an input to the digital band pass filter 41. The digital band pass filter is an adjustable band pass filter having a relatively high Q, i.e., about 150, whose pass band is adjustable as a function of the frequency of the clock signal appearing at the lead 150. The band pass filter suitably comprises an MC 145433 chip, with clock input at pin 7. The center of the pass band defined by the digital band pass filter 41 is faithfully maintained by the clock signal at the exciter test frequency.

The function of the digital band pass filter 41 is to further reduce interference from the nearby electromagnetic induction annealing fields. Accordingly, the digital band pass filter is placed in series with and upstream from a demodulator circuit 156.

The detector circuitry 30 receives an input on a lead 158 from exciter power amplifier 28. This input is directed in parallel to test coil balancing circuitry 160 and to reference phase circuitry 162. The balancing circuitry 160 is a manual balance controlled by an amplitude adjustment potentiometer 161 and a phase adjustment potentiometer 163. The balance circuit provides an output to a balance pre-amp 168. At setup, when no workpiece flaw is present, the potentiometers 161, 163 are set to null out, in the balance pre-amp, noise and imbalance in the signal from the differential coil, which is received at the balance pre-amp over a lead 170.

The detector coil output to the balance pre-amp is over the lead 170. The lead 170 carries the characteristic carrier and flaw indicating signals from the detector coil of the test probe representing detected defects in the pipe passing by the detector coil. These flaw indicating signals are amplified in the pre-amp circuitry 168, and passed through the band pass filter 41 as an input to the demodulator 156.

Another input to the detector component is from the reference phase circuitry 162. The demodulator component 156 compares the phase of the signal over the lead 170 (amplified in pre-amp 168) with the fixed reference phase from the circuiry 162. The flaw signal, being mainly characterized by a phase change, is thus easily detectable against a reference phase.

A phase adjusting potentiometer 165 adjusts the reference phase as desired to produce a null signal in the absence of a defect indicating signal over the lead 170.

Details of the balancing circuitry 30 and balancing method are set forth in U.S. Pat. No. 3,916,301, columns 4 et seq.

From the detector output over the lead 40, the flaw indicating signals are transmitted to the trim loss detector 70, anneal temperature monitor 64, test signal processor 50 and signal verifier circuitry 52, for subsequent processing as already described above. Likewise, the test probe cooling monitor 80, indicator 82, encoder 84 and encoder control circuitry 86 function in the manner described above.

It is to be understood that the description of the specific embodiment of this invention set forth herein is intended as illustrative, rather than exhaustive, of the invention. Those of ordinary skill in the relevant art may make certain additions, deletions or modifications with respect to the embodiment described herein without departing from the spirit or the scope of this invention, as defined in the appended claims.

I claim:

1. A weld flaw detection system for use in connection with welded workpiece manufacturing apparatus incorporating circuitry and apparatus for induction annealing of welds by the production of strong alternating electromagnetic annealing fields in a region of the weld, said flaw detection system comprising:
   (a) exciter circuitry capable of generating alternating test eddy currents in a workpiece at a carrier frequency;
   (b) detection circuitry including a demodulator for detecting variation in eddy currents to produce a flaw signal modulated on the carrier frequency indicating presence of a workpiece weld defect;
   (c) control circuitry for varying the frequency of the induction annealing electromagnetic field, and
   (d) regulation circuitry for adjusting the alternating carrier frequency of said test eddy currents as a function of the induction annealing field frequency.

2. The system of claim 1, wherein:
said regulation circuitry includes circuitry for maintaining said test eddy current carrier frequency as a non-integral multiple of said induction annealing field frequency.

3. The system of claim 2, wherein:
said regulation circuitry maintains said test eddy current carrier frequency at a multiple of approximately of 4.5 times the induction annealing field frequency.

4. The system of claim 1, further comprising:
a second ultrasonic pipe testing system for providing additional flaw detection.

5. The system of claim 1, further comprising:
   (a) an electrical filter interposed in the detection circuitry for selectively passing electrical signals having frequencies lying within a predetermined range, and
   (b) means for adjusting said frequency range of said filter as a function of the induction annealing field frequency.

6. The system of claim 5, wherein:
said electrical filter comprises a band pass filter defining a pass band.

7. The system of claim 6, wherein:
said range adjusting circuitry for said filter comprises circuitry for centering the pass band of said filter at approximately the carrier frequency.

8. The system of claim 7, wherein said electrical filter comprises a digital band pass filter.

9. The system of claim 1, further comprising:
circuitry responsive to turn-on of the annealing circuitry for disabling said frequency adjustment circuitry for a predetermined time.

10. The system of claim 1, wherein:
said regulation circuitry includes means for adjusting said carrier frequency to a predetermined value in the absence of an induction annealing field frequency.

11. The system of claim 1, further comprising:
circuitry coupled to the detector circuitry for producing a signal indicating temperature of a region of the pipe.

12. An eddy current pipe weld flaw detector system for evaluating the quality of pipe welds annealed by electrical induction heating, past which a pipe is propelled along a path, said system comprising:
   (a) exciter circuitry for producing eddy currents within a pipe propelled along the path;
   (b) detector circuitry for sensing defects in said pipe as evidenced by variations in the eddy currents produced by the exciter circuitry;
   (c) said exciter and detection circuitry comprising exciter and detector coils, respectively, both located along the path downstream of and proximate the annealing circuitry;
   (d) an enclosure at least partially surrounding said exciter and detector coils containing a liquid coolant for cooling said coils;
   (e) means for sensing the level of said coolant, and
   (f) means coupled to the coolant level sensor means for producing an indication in response to the coolant level falling below a predetermined value.

13. A system for testing hot annealed pipe welds by the use of eddy currents, said system comprising:
   (a) a test probe including:
      (i) an exciter coil, and
      (ii) a detector coil;
   (b) means for relatively moving a pipe with respect to the probe along a path near the coils;
   (c) circuitry for causing the exciter coil to induce eddy currents in a pipe when moving along the path;
   (d) circuitry coupled to the detector coil for sensing defects in a tested pipe in response to variations in said eddy currents;
   (e) means for sensing the temperature proximate the tested zone of such a pipe, said temperature sensing means comprising said detector coil circuitry being coupled for sensing resistivity of a portion of the pipe independently of direction of an electromagnetic field through said workpiece.

14. The system of claim 13, wherein:
   (a) said detector coil is differentially wound, and
   (b) said resistivity measuring circuitry comprises circuitry for sensing the degree of imbalance produced by said differentially wound coil.

15. The system of claim 13, wherein:
said temperature measuring means comprises circuitry for sensing resistivity of a portion of the pipe.

16. The system of claim 15, wherein:
   (a) said detector coil is differentially wound, and
   (b) said resistivity measuring circuitry comprises circuitry for sensing the degree of imbalance produced by said differentially wound coil.

17. A pipe processing system comprising:
   (a) apparatus for forming strip metal into a generally cylindrical shape, defining a longitudinal seam;
   (b) apparatus for moving the formed metal longitudinally along a path;
   (c) apparatus downstream along said path from said forming apparatus for effecting a weld along a seam;
   (d) induction annealing apparatus and circuitry downstream along said path from said welding apparatus for annealing a seam weld by induction heating at a first alternating frequency;
(e) a test probe comprising:
(i) an exciter coil, and
(ii) circuitry coupled to the exciter coil for inducing eddy currents in a region of an annealed welded seam at a second alternating frequency which is a nonintegral multiple of said first frequency;
(iii) said probe being located downstream along the path from said annealing circuitry and apparatus and at a location at which the temperature of an annealed weld region of a pipe being tested is above the Curie temperature for the pipe material;
(f) detection circuitry for producing indications of defects in a pipe weld region moved along the path in response to variations in said eddy currents, and
(g) a supplementary test apparatus for detecting flaws in a pipe downstream along the path from said detector probe by the use of ultrasonic energy.

18. A hot annealed pipe weld flaw detection system for use in connection with electrical induction weld annealing apparatus and circuitry which anneals the pipe weld by the use of strong alternating electromagnetic fields having a first frequency, said system comprising:
(a) exciter circuitry located proximate the annealer apparatus for producing eddy currents in a pipe when near the exciter circuitry at a second frequency which is a non-integral multiple of said first frequency, and
(b) detector circuitry responsive to variations in the eddy currents generated by said exciter circuitry to provide indication of flaws in a tested pipe.

19. A system for detecting defects in a metallic workpiece wherein such workpiece, during its production, is subject to acquisition of a series of discrete defects approximately uniformly spaced along the workpiece, said system comprising:
(a) apparatus adapted to propel a workpiece along a path extending past at least a portion of the detector system;
(b) a detector probe for producing an indication of a defect each time a defect passes by the probe, and
(c) discrimination circuitry for producing a recurrent flaw indicating signal only in response to the occurrence of a series of defect indicating signals at approximately a predetermined frequency for a predetermined length of time.

20. The system of claim 19, wherein said discrimination circuitry produces a recurrent flaw signal in response to the occurrence of defect indicating signals at a frequency of about 30 to 90 Hz.

21. A pipe weld quality testing method for use in connection with welded pipe manufacturing apparatus and alternating induction weld annealing equipment, said method comprising the steps of:
(a) generating alternating test eddy currents in a pipe subsequent to the induction annealing;
(b) producing a signal indicating a defect in the pipe in response to a variation in said test eddy currents;
(c) varying the frequency of the induction annealing field, and
(d) adjusting the frequency of said test eddy currents as a function of the induction annealing field frequency.

22. The method of claim 21, wherein:
said frequency adjustment step comprises maintaining said test eddy current frequency at a non-integral multiple of the induction annealing field frequency.

23. The method of claim 22, wherein:
said frequency adjustment step comprises maintaining said test eddy current frequency at a multiple of approximately 4.5 times the induction annealing field frequency.

24. The method of claim 21, further comprising the step of:
ultrasonically testing the pipe for defects.

25. The method of claim 21, wherein:
(a) said detection step includes filtering electrical signals having frequencies lying outside of a predetermined pass band, and
(b) said method further comprises the step of adjusting the pass band as a function of the induction annealing field frequency.

26. The method of claim 25, wherein:
said pass band adjustment step comprises centering the pass band at approximately the eddy current test frequency.

27. The method of claim 21, further comprising the step of:
refraining from execution of said frequency adjustment step for a predetermined time following turn on of said induction annealing equipment.

28. The method of claim 21, further comprising the step of:
adjusting said exciter test eddy current frequency to a predetermined value in the absence of an induction annealing field frequency.

29. The method of claim 21, further comprising the step of:
producing a signal indicating temperature of a tested region of the pipe.

30. The method of claim 21, wherein:
said eddy current generation and defect detection steps are performed with respect to a region of a pipe having a temperature in excess of its Curie temperature.

31. The method of claim 21, wherein said step of producing a defect indicating signal comprises:
producing indications of pipe flaws only in response to waveforms having predetermined polarity sequence characteristics.

32. A hot annealed pipe weld flaw detection method for use in connection with electrical induction weld annealing apparatus producing induction annealing fields at a first frequency, said method comprising the steps of:
(a) producing eddy currents at varying locations in a pipe at a second frequency which is a non-integral multiple of said first frequency; and
(b) producing indication of flaws in the pipe in response to variations in said test eddy currents.

33. A method for detecting defects in a metallic workpiece wherein the workpiece, during its production, is subject to acquisition of series of discrete similar defects spaced along a portion of the workpiece, said method comprising the steps of:
(a) propelling a workpiece along the path extending past at least a portion of the detector system comprising a probe;
(b) producing an indication of a defect each time a defect passes by the probe, and
(c) producing a recurrent flaw indicating signal only in response to the recurrence of defect indications in a predetermined frequency range for a predetermined length of time.

34. A pipe weld flaw detection system for use in connection with welded pipe manufacturing apparatus incorporating circuitry and apparatus for induction annealing of pipe welds by the production of strong alternating electromagnetic fields in a region of the pipe weld, said flaw detection system comprising:
 (a) exciter circuitry adapted for generating alternating test eddy currents in a pipe at a carrier frequency;
 (b) circuitry, including a differentially wound detection coil, for detecting variation in eddy currents to produce a flaw indicating signal;
 (c) apparatus for moving a pipe along a path relative to and proximate the detection circuitry;
 (d) circuitry for varying the frequency of the induction annealing electromagnetic fields;
 (e) circuitry for adjusting the carrier frequency of said test eddy currents as a function of the induction annealing field frequency, said adjustment circuitry maintaining the carrier frequency at a non-integral multiple of the annealing frequency and approximately centered between successive harmonics of the annealing frequency;
 (f) signal verification circuitry responsive to only those flaw indicating signals having predetermined polarity sequence characteristics;
 (g) apparatus and circuitry for monitoring temperature of a pipe weld when located in the region of the detection coil;
 (h) an adjustable band pass filter coupled to said detection coil for reduction of interference;
 (i) circuitry responsive to the annealer frequency to maintain the pass band of the adjustable filter centered at approximately the carrier frequency;
 (j) a marker located downstream from said detection coil;
 (k) marker delay circuitry for actuating the marker capable of marking a workpiece at a predetermined delay increment following occurrence of a flaw indicating signal;
 (l) means for sensing velocity of relative movement between the detector coil and a workpiece, and
 (m) circuitry for adjusting the marker delay time as a function of said sensed velocity.

35. A system for detecting flaws in metallic workpieces, said system comprising:
 (a) a test probe;
 (b) apparatus capable of effecting relative motion between a workpiece and the test probe;
 (c) circuitry associated with the test probe for producing a flaw indicating signal modulated upon a carrier frequency in response to passage of a workpiece flaw past the test probe;
 (d) a demodulator coupled to said probe associated circuitry for detecting the flaw indicating signal;
 (e) an adjustable band pass electrical filter interposed between said demodulator and said associated circuitry, and
 (f) circuitry responsive to the carrier frequency for maintaining the pass band of the adjustable filter centered approximately upon the carrier frequency.

36. A weld flaw detection system for use in connection with welded workpiece manufacturing apparatus incorporating circuitry and apparatus for induction annealing of welds by the production of strong alternating electromagnetic annealing fields in a region of the weld and including means for adjusting the frequency of said strong alternating electromagnetic annealing fields, said flaw detection system comprising:
 (a) exciter circuitry capable of generating alternating test eddy currents in a workpiece at a carrier frequency;
 (b) detection circuitry including a demodulator for detecting variation in eddy currents to produce a flaw signal modulated on the carrier frequency indicating presence of a workpiece weld defect, and
 (c) regulation circuitry for adjusting the alternating carrier frequency of said test eddy currents as a function of the induction annealing field frequency.

37. A method of eddy current testing of metallic workpieces, said method comprising the steps of:
 (a) inducing eddy current flow in a workpiece by use of a test probe;
 (b) relatively moving the workpiece with respect to the probe along a path;
 (c) producing a workpiece flaw indication in response to a nonuniformity in the eddy currents, and
 (d) measuring the temperature proximate the tested region of the workpiece by sensing the resistivity of a portion of the workpiece independently of transmission of electromagnetic fields through said workpiece by the use of detector coil circuitry.

38. The method of claim 37, wherein said step of producing a defect indicating signal comprises:
 producing indications of pipe flaws only in response to waveforms having predetermined polarity sequence characteristics.

* * * * *